United States Patent [19]

Grambow et al.

[11] 4,321,113

[45] Mar. 23, 1982

[54] ELECTRONIC CALIBRATION OF ELECTROCHEMICAL SENSORS

[75] Inventors: Lutz Grambow; Dieter Krüger, both of Lübeck, Fed. Rep. of Germany

[73] Assignee: Drägerwerk AG, Fed. Rep. of Germany

[21] Appl. No.: 168,663

[22] Filed: Jul. 11, 1980

[30] Foreign Application Priority Data

Jul. 20, 1979 [DE] Fed. Rep. of Germany ....... 2929387

[51] Int. Cl.³ .................. G01N 27/52; G12B 13/00
[52] U.S. Cl. ........................ 204/1 T; 73/1 G; 128/635; 204/195 R; 364/571
[58] Field of Search ............... 204/1 K, 1 T, 195 R; 73/1 G; 364/571; 128/635

[56] References Cited

U.S. PATENT DOCUMENTS 3,852,169 12/1974 Kring et al. .................. 204/1 T
4,218,746  8/1980 Koshiishi ...................... 364/571

FOREIGN PATENT DOCUMENTS 2431194 12/1976 Fed. Rep. of Germany .

Primary Examiner—G. L. Kaplan
Attorney, Agent, or Firm—McGlew and Tuttle

[57] ABSTRACT

An arrangement and method is provided for electronically calibrating electrochemical sensors for determining partial pressures in physiological media. In an electrochemical sensor arrangement for sensing such partial pressures, a working electrode with an electropotential which varies relative to time is calibrated by varying the limit oxygen reduction current thereof as a function of the quotient of the potential of a calibration electrode and the measured potential of the working electrode.

5 Claims, 1 Drawing Figure

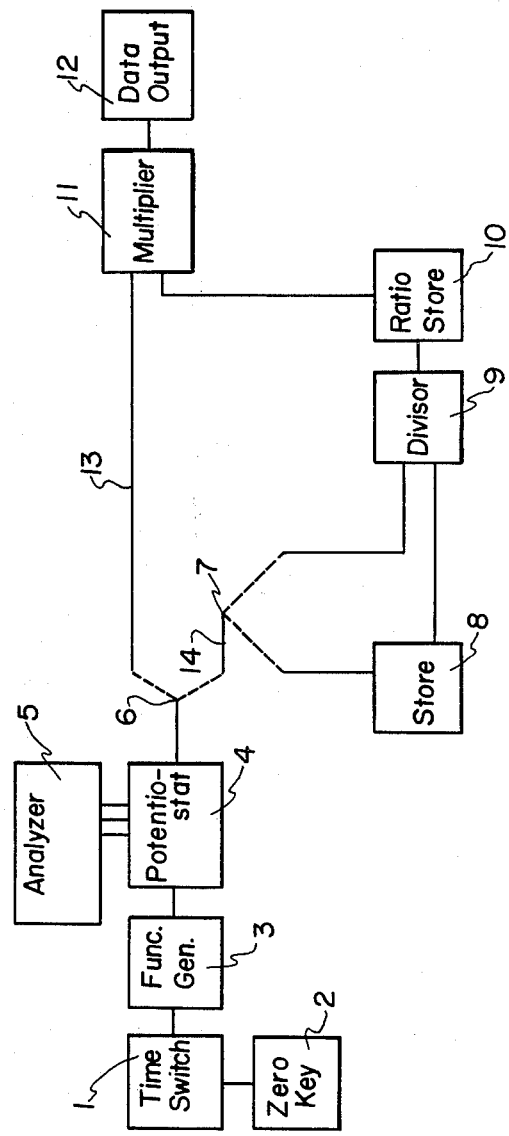

ELECTRONIC CALIBRATION OF ELECTROCHEMICAL SENSORS

BACKGROUND OF THE INVENTION

The invention relates, in general, to the electronic calibration and, more particularly, to a new and useful arrangement and technique for the electrical calibration of electrochemical sensors for determining partial pressures in physiological media.

Polarography is an electrometric method of chemical analysis that is based on the current voltage relationship at a special type of electrode. Potentiostatic and polarographic sensors operate with a constant potential. In the case of air-saturated aqueous electrolytes, the potential is preferably in the potential range 0.7 to 1.5 V relative to a reference hydrogen electrode in the same solution. In this potential range, oxidizable gases, such as CO, $H_2S$, NO, $SO_2$ and the like, are oxidized without being influenced, respectively, by the currents of the oxygen reduction or oxygen evolution. The electrode current, moreover, is proportional to the concentration of the ions of the substance to be measured. The activity of the working electrode, moreover, increases with the time. The sensors must, therefore, be checked and calibrated about once a week.

If the activity of a freshly calibrated working electrode is Ao, and the activity at a measuring time t is A, then the activity ratio Ao/A yields a factor for determining the remaining output activity at a time t.

A known arrangement (see West German Pat. No. 2,431,194) for determining the partial pressure of gases which are dissolved in physiological media includes an electrode catheter having flushing channel plus flushing medium for the electrode surface. In addition, an electrical correction device is assigned to the electrode catheter. In operation, the top of the catheter is principally flushed with the flushing medium in the rhythm of a time switch or calibration, or it is surrounded by the body fluid to be measured. During the calibration phase, that is, when flushing with the flushing medium, the electrode sensitivity is determined in respect to a standard known value. During the subsequent measuring phase, the measured value is corrected by the still existing electrode sensitivity, so that a corrected partial pressure of the gas to be measured is obtained. A disadvantage of the known arrangement is that the automatic but complicated continuous correction of the measured value over the standard value must be determined anew before each measurement. For this purpose, a special flushing medium must be continuously made available.

SUMMARY OF THE INVENTION

It is an object of the present invention to provide automatic determination and compensation of time related variations in the activity of the working electrode of potentiostatic or polarographic sensors having test gas or calibration solutions so that the calibration intervals can be considerably extended.

To permit a simple arrangement, the invention utilizes the fact that the activity ratio Ao/A is applicable not only to the measuring range, the potential range 0.7-1.5 V relative to a standard or reference hydrogen electrode in the same solution, but also to the oxygen reduction limiting current range. The activity range determined by the reduction potential $\phi$ red=0.35 V. The atmospheric oxygen content which can be considered as constant, ensures accurate data. Making the corresponding voltages available and switching between the measuring and calibrating circuits are known from the state of the art.

Thus, it is an object of the invention to provide in an electrochemical sensor arrangement for sensing the partial pressure of gases of the type having a working electrode with an electrode potential which varies relative to time, and improved means for calibrating the arrangement. The improvement includes a calibration electrode having an electrode potential equal to that of the working electrode, a function generator operable to decompose an oxide coating on the working electrode to generate a limiting oxygen reduction current, timer means for periodically starting the operation of the function generator, means for measuring the limiting oxygen reduction current, means for measuring the potential of the calibration electrode, means for measuring the potential of the working electrode, means for dividing the potential of the calibration electrode by the potential of the working electrode to attain a quotient, and means for multiplying the quotient and delimiting oxygen reduction current to obtain a corrected data output.

It is a further object of the invention to provide in a method for determining the partial pressure of gases using an electrochemical sensor having a working electrode within an electropotential which varies relative to time, an improved method of correcting the potential signal generated by the working electrode comprising measuring the potential of a calibration electrode, measuring the potential of the working electrode, measuring the limiting oxygen reduction current of the working electrode, and adjusting the measured limiting oxygen reduction current of the working electrode by multiplying the value thereof by the quotient of the potential of the calibration electrode and the potential of the working electrode.

It is a further object of the invention to provide an improved calibration arrangement of the type described which is simple in design, rugged in construction and economical to manufacture.

For an understanding of the principles of the invention, reference is made to the following description of a typical embodiment thereof as illustrated in the accompanying drawings.

BRIEF DESCRIPTION OF THE DRAWINGS

The sole drawing is a block circuit diagram of an arrangement according to the invention.

DETAILED DESCRIPTION

The invention may be described in detail in connection with the potentiostatic sensor for measuring carbon monoxide. The basic idea starts from the consideration that the activity ratio Ao/A is applicable not only to the potential range 0.7-1.5 V, relative to a reference hydrogen electrode in the same solution, but also to the oxygen reduction limit current range. In order to determine the activity ratio Ao/A, the potential of the working electrode changes, in this example, from the measuring potential $\phi$ M=0.95 V, relative to a reference hydrogen electrode in CO-oxidation on platinum in 8 n $H_2SO_4$, to a potential in the oxygen reduction limit current range of $\phi$ red=0.35 V relative to the reference hydrogen electrode and the diffusion current is then measured.

A time switch 1, having a zero-key 2, starts a potential-time program daily in a function generator 3. Function generator 3 controls potentiostat 4 with analyzer 5. The program is based on three stages:

(a) the reduction potential $\phi = 0.35$ V relative to the reference hydrogen electrode for 3 min; during this time, the oxide coating of the working electrode is decomposed, so that the constant oxygen reduction-limit current is obtained;

(b) the oxide forming potential $\phi$ OX=1.5 V for 3 min; during this time, the oxide coating is regenerated on the electrode;

(c) the measuring potential $\phi$ M=0.95 V for CO.

Together with the start of the function generator 3, switch 6 switches from measuring circuit 13 to calibration circuit 14.

For determining the activity ratio Ao/A, it is necessary to determine the activity Ao and the activity A in calibration circuit 14.

For the activity Ao, the diffusion-limit current, which results with the reduction potential from the first measurement after calibration with a test gas or calibration substance, is stored through the corresponding position of switch 7 in store 8.

For the active A, the subsequent diffusion currents are fed to divisor 9 after switching switch 7. Divisor 9 has the contents of store 8 available.

A ratio store 10 receives the signal Ao/A appearing at the output of divisor 9. At program stage c of function generator 3, switch 6 switches back to measuring circuit 13. The output signal of potentiostat 4 and the contents of ratio store 10 are fed to multiplier 11. The calibrated signal is available to data output 12.

While a specific embodiment of the invention has been shown and described in detail to illustrate the application of the principles of the invention, it will be understood that the invention may be embodied otherwise without departing from such principles.

What is claimed is:

1. In an electrochemical sensor arrangement for sensing the partial pressure of gases of the type having a working electrode with an electrode potential which varies relative to time, an improved means for calibrating the arrangement comprising a calibrator electrode having an electrode potential equal to that of the working electrode, a function generator operable to decompose an oxide coating on the working electrode to generate a limiting oxygen reduction current, timer means for periodically starting the operation of the function generator, means for measuring the limiting oxygen reduction current, means for measuring the potential of the calibration electrode, means for measuring the potential of the working electrode, means for dividing the potential of the calibration electrode by the potential of the working electrode to obtain a quotient, and means for multiplying the quotient and the limiting oxygen reduction current to obtain a current data output.

2. The improvement as set forth in claim 1, wherein said timer means is operable to start said function generator once daily.

3. The improvement as set forth in claim 1, wherein said function generator is operable to regenerate an oxide coating on said working electrode.

4. The improvement as set forth in claim 1, further comprising means for storing said quotient.

5. In a method for determining the partial pressure of gases using an electrochemical sensor having a working electrode with an electrode potential which varies relative to time, the improved method of correcting a potential signal generated by the electrode comprising measuring the potential of a calibration electrode, measuring the potential of the working electrode, measuring the limit oxygen reduction current of the working electrode, and adjusting the measured limit oxygen reduction current of the working electrode by multiplying the value thereof by the quotient of the potential of the calibration electrode and the potential of the working electrode.

* * * * *